United States Patent
Smith (10) Patent No.: US 9,149,178 B2
(45) Date of Patent: Oct. 6, 2015

(54) SURGICAL ACCESS ASSEMBLY AND METHOD OF USE THEREFOR

(71) Applicant: Covidien LP, Mansfield, MA (US)

(72) Inventor: Robert C. Smith, Middlefield, CT (US)

(73) Assignee: Covidien LP, Mansfield, MA (US)

(*) Notice: Subject to any disclaimer, the term of this patent is extended or adjusted under 35 U.S.C. 154(b) by 0 days.

(21) Appl. No.: 13/782,057

(22) Filed: Mar. 1, 2013

(65) Prior Publication Data

US 2013/0253278 A1      Sep. 26, 2013

Related U.S. Application Data

(60) Provisional application No. 61/615,504, filed on Mar. 26, 2012.

(51) Int. Cl.
| | |
|---|---|
| *A61B 1/32* | (2006.01) |
| *A61B 17/34* | (2006.01) |
| *A61B 17/02* | (2006.01) |
| *A61M 39/02* | (2006.01) |
| *A61B 17/00* | (2006.01) |

(52) U.S. Cl.
CPC ............... *A61B 1/32* (2013.01); *A61B 17/0293* (2013.01); *A61B 17/3423* (2013.01); *A61M 39/0247* (2013.01); *A61B 2017/00477* (2013.01); *A61M 2039/0261* (2013.01); *A61M 2039/0279* (2013.01)

(58) Field of Classification Search
CPC ................ A61B 17/3423; A61B 1/32; A61M 2039/0261; A61M 2039/0279; A61M 2017/00477

USPC ........ 600/37, 29, 30, 201–246, 114; 128/899; 604/26, 204–208, 513, 264, 539; 606/1, 108, 213

See application file for complete search history.

(56) References Cited

U.S. PATENT DOCUMENTS

| | | |
|---|---|---|
| 4,183,357 A | 1/1980 | Bentley et al. |
| 5,366,478 A | 11/1994 | Brinkerhoff et al. |
| 5,524,644 A | 6/1996 | Crook |
| 5,906,577 A | 5/1999 | Beane et al. |
| 6,033,428 A | 3/2000 | Sardella |
| 6,254,534 B1 | 7/2001 | Butler et al. |
| 6,382,211 B1 | 5/2002 | Crook |
| 6,450,983 B1 | 9/2002 | Rambo |
| 6,582,364 B2 | 6/2003 | Butler et al. |
| 6,589,167 B1 | 7/2003 | Shimomura et al. |
| 6,613,952 B2 | 9/2003 | Rambo |

(Continued)

FOREIGN PATENT DOCUMENTS

| | | |
|---|---|---|
| DE | 202011003066 U1 | 4/2011 |
| EP | 0950376 A1 | 10/1999 |

(Continued)

OTHER PUBLICATIONS

European Search Report from EP 13160757 dated Jun. 10, 2014.

*Primary Examiner* — Pedro Philogene (57) ABSTRACT

A surgical access assembly includes an access port and a seal anchor. The access port includes first and second rings and a sleeve extending between the first and second rings. In particular, the sleeve includes an inner surface having an attaching member. The seal anchor is adapted to be at least partially disposed in the access port. The seal anchor includes a base portion configured to detachably engage the attaching member of the access port.

18 Claims, 9 Drawing Sheets

(56) References Cited

U.S. PATENT DOCUMENTS

| | | |
|---|---|---|
| 6,723,044 B2 | 4/2004 | Pulford et al. |
| 6,846,287 B2 | 1/2005 | Bonadio et al. |
| 6,939,296 B2 | 9/2005 | Ewers et al. |
| 6,945,932 B1 | 9/2005 | Caldwell et al. |
| 6,958,037 B2 | 10/2005 | Ewers et al. |
| 7,033,319 B2 | 4/2006 | Pulford et al. |
| 7,081,089 B2 | 7/2006 | Bonadio et al. |
| 7,163,510 B2 | 1/2007 | Kahle et al. |
| 7,195,590 B2 | 3/2007 | Butler et al. |
| 7,238,154 B2 | 7/2007 | Ewers et al. |
| 7,344,547 B2 | 3/2008 | Piskun |
| 7,377,898 B2 | 5/2008 | Ewers et al. |
| 7,445,597 B2 | 11/2008 | Butler et al. |
| 7,473,221 B2 | 1/2009 | Ewers et al. |
| 7,540,839 B2 | 6/2009 | Butler et al. |
| 7,650,887 B2 | 1/2010 | Nguyen et al. |
| 7,704,207 B2 | 4/2010 | Albrecht et al. |
| 7,727,146 B2 | 6/2010 | Albrecht et al. |
| 7,766,824 B2 | 8/2010 | Jensen et al. |
| 8,021,296 B2 * | 9/2011 | Bonadio et al. ............... 600/208 |
| 8,343,047 B2 | 1/2013 | Albrecht et al. |
| 8,357,085 B2 * | 1/2013 | Shelton et al. ............... 600/208 |
| 8,517,995 B2 * | 8/2013 | Voegele et al. ............... 604/175 |
| 2003/0187376 A1 | 10/2003 | Rambo |
| 2004/0092795 A1 | 5/2004 | Bonadio et al. |
| 2005/0020884 A1 | 1/2005 | Hart et al. |
| 2005/0148823 A1 | 7/2005 | Vaugh et al. |
| 2005/0192483 A1 | 9/2005 | Bonadio et al. |
| 2006/0161050 A1 | 7/2006 | Butler et al. |
| 2006/0247498 A1 | 11/2006 | Bonadio et al. |
| 2006/0258899 A1 * | 11/2006 | Gill et al. ....................... 600/37 |
| 2007/0093695 A1 | 4/2007 | Bonadio et al. |
| 2007/0118175 A1 | 5/2007 | Butler et al. |
| 2007/0151566 A1 | 7/2007 | Kahle et al. |
| 2007/0162067 A1 * | 7/2007 | Lunsford et al. ............... 606/192 |
| 2007/0203398 A1 | 8/2007 | Bonadio et al. |
| 2007/0208312 A1 | 9/2007 | Norton et al. |
| 2007/0270654 A1 | 11/2007 | Pignato et al. |
| 2008/0021360 A1 | 1/2008 | Fihe et al. |
| 2009/0221966 A1 * | 9/2009 | Richard ................... 604/164.04 |
| 2010/0240960 A1 | 9/2010 | Richard |
| 2010/0249694 A1 | 9/2010 | Choi et al. |
| 2010/0286484 A1 | 11/2010 | Stellon et al. |
| 2010/0312062 A1 * | 12/2010 | Cropper et al. ............... 600/204 |
| 2011/0054260 A1 | 3/2011 | Albrecht et al. |
| 2011/0071359 A1 | 3/2011 | Bonadio et al. |
| 2011/0125186 A1 | 5/2011 | Fowler et al. |
| 2011/0251464 A1 | 10/2011 | Kleyman |
| 2011/0260449 A1 * | 10/2011 | Pokorney ....................... 285/321 |
| 2012/0130177 A1 | 5/2012 | Davis |
| 2012/0209078 A1 | 8/2012 | Pribanic et al. |
| 2012/0245427 A1 | 9/2012 | Kleyman |
| 2012/0245429 A1 | 9/2012 | Smith |
| 2012/0245430 A1 | 9/2012 | Kleyman et al. |
| 2012/0253136 A1 * | 10/2012 | Rodrigues, Jr. ............... 600/208 |
| 2012/0283520 A1 | 11/2012 | Kleyman |

FOREIGN PATENT DOCUMENTS

| | | |
|---|---|---|
| EP | 2181657 A2 | 5/2010 |
| EP | 2238933 A1 | 10/2010 |
| EP | 2248478 A1 | 11/2010 |
| WO | WO 96/10963 | 4/1996 |
| WO | WO 00/32116 | 6/2000 |
| WO | WO 00/54675 | 9/2000 |
| WO | WO 2004/075741 A2 | 9/2004 |
| WO | WO 2006/110733 A2 | 10/2006 |
| WO | WO 2010/141409 A1 | 12/2010 |
| WO | WO 2010/141673 A1 | 12/2010 |

* cited by examiner

SURGICAL ACCESS ASSEMBLY AND METHOD OF USE THEREFOR

CROSS REFERENCE TO RELATED APPLICATION

The present application claims the benefit of and priority to U.S. Provisional Application Ser. No. 61/615,504, filed on Mar. 26, 2012, the entire contents of which are incorporated herein by reference.

BACKGROUND

1. Technical Field

The present disclosure relates to a surgical access assembly, and more particularly, to a surgical access assembly including an access port and a seal anchor detachably engaging each other in a sealing relation and a method of use therefor.

2. Background of Related Art

Various surgical procedures are performed in a minimally invasive manner. This includes forming a small opening through a body wall of the patient, e.g., in the abdomen, and inserting a seal anchor through the opening to provide a substantially fluid-tight seal between a body cavity of a patient and the atmosphere. Due to the relatively small interior dimensions of the access devices used in endoscopic procedures, only the elongated, small diametered instrumentation such as, e.g., trocar and cannula assemblies, may be used to access the internal body cavities and organs. In general, prior to the introduction of the surgical object into the patient's body, insufflation gases are used to enlarge the area surrounding the target surgical site to create a larger, more accessible work area.

When compared to the larger incisions typically found in traditional procedures, both trauma to the patient and recovery time are reduced for procedures involving small incisions. However, minimally invasive surgery such as, e.g., laparoscopy, has several limitations. In particular, surgery of this type requires a great deal of skill in manipulating the long narrow endoscopic instruments to a remote site under endoscopic visualization. To this end, hand-assisted laparoscopic techniques and procedures have been developed. These procedures include both laparoscopic and conventional surgical methodologies. The hand-assisted technique is performed utilizing a seal anchor in conjunction with an access port, which is an enlarged device that protects the opening from, for example, infection and contamination.

The maintenance of a substantially fluid-tight seal is desirable to prevent the escape of the insufflation gases and the deflation or collapse of the enlarged surgical site. Accordingly, there is a need for an access assembly used in a hand-assisted minimally invasive procedure that can accommodate a variety of surgical objects while maintaining the integrity of an insufflated workspace.

SUMMARY

In accordance with an embodiment of the present disclosure, there is provided a surgical access assembly including an access port and a seal anchor. The access port includes first and second rings and a sleeve extending between the first and second rings. The sleeve includes an inner surface having an attaching member. The seal anchor is adapted to be at least partially disposed in the access port. The seal anchor includes a base portion configured to detachably engage the attaching member of the access port.

The base portion of the seal anchor may include a second attaching member adapted to be detachably attached to the attaching member of the access port. The attaching member of the access port and the second attaching member of the seal anchor may be a refastenable tape or a hook and loop fastener. Alternatively, at least one of the attaching member of the access port and the second attaching member of the seal anchor may be an adhesive tape.

The attaching member may be an annular ring disposed on the inner surface of the sleeve. The base portion of the seal anchor may define a groove configured to receive therein the second attaching member of the seal anchor. Under such configuration, the second attaching member of the seal anchor may be an annular member peripherally arranged about the lumen defined in the seal anchor. In addition, the second attaching member of the seal anchor may define a slit in alignment with the lumen. The seal anchor may define a lumen dimensioned to receive surgical instruments therethrough.

The first ring of the access port may have a kidney shaped cross-sectional profile, and the second ring of the access port may be an O-ring. Furthermore, the second ring may be an inflatable balloon. The first and second rings may be elastic. In particular, the seal anchor may be made of a compressible material. It is also contemplated that the attaching member of the access port may extend along a length of the sleeve of the access port.

In accordance with another aspect of the present disclosure, there is provided a method of accessing an internal body cavity including providing a surgical access assembly including an access port and a seal anchor. In particular, the access port includes first and second rings and a sleeve extending between the first and second rings. The sleeve includes an inner surface having an attaching member. In addition, the seal anchor is adapted to be at least partially disposed in the access port. The seal anchor includes a base portion including a second attaching member corresponding to the attaching member of the access port. The method further includes positioning a first ring of the access port into the body cavity, rolling the sleeve of the access port about the second ring such that the first and second rings engage an internal peritoneal wall of tissue and an outer epidermal tissue, respectively, positioning the seal anchor at least partially within the access port in a sealing relation therewith, and introducing a surgical instrument to the body cavity through the seal anchor.

In another embodiment, positioning the seal anchor at least partially within the access port may include placing the seal anchor within the second ring and aligning the second attaching member of the seal anchor with the attaching member of the access port. In addition, positioning the seal anchor at least partially within the access port may also include placing the seal anchor on the outer epidermal tissue. It is further contemplated that the method may further include insufflating the body cavity.

BRIEF DESCRIPTION OF THE DRAWINGS

Various embodiments of the present disclosure are described hereinbelow with reference to the drawings, wherein.

DETAILED DESCRIPTION OF EMBODIMENTS

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail.

Figure 1:
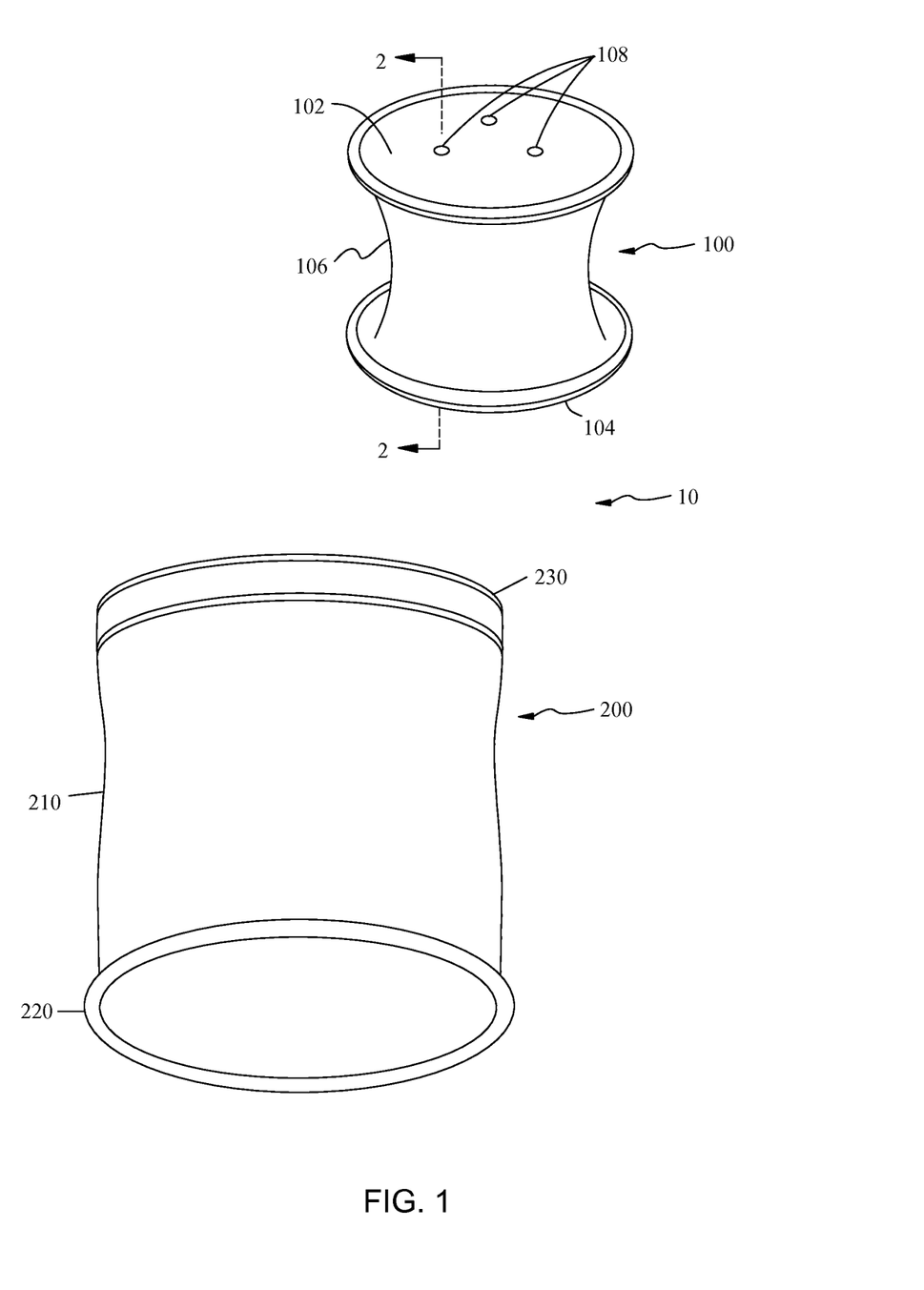
FIG. 1 is a perspective view of a surgical access assembly in accordance with an embodiment of the present disclosure.

With reference to FIG. 1, there is illustrated a surgical access assembly 10 in accordance with an embodiment of the present disclosure. Surgical access assembly 10 includes a seal anchor 100 and an access port 200. Access port 200 is adapted for insertion within a tissue tract, e.g., through an opening in the abdominal or peritoneal lining, as well as a naturally occurring orifice. Access port 200 protects the opening from, for example, infection and contamination. In addition, access port 200 may serve to retract the opening, as will be discussed below. Seal anchor 100 is detachably attached to and at least partially disposed in access port 200 to provide a substantially fluid-tight seal between a body cavity of a patient and the atmosphere. Both access port 200 and seal anchor 100, however, may be used as a stand-alone device for insertion of endoscopic instruments.

With continued reference to FIG. 1, seal anchor 100 is configured to receive surgical instruments of varying diameter therethrough. Seal anchor 100 is formed from elastic/compressible type material having sufficient compliance to form a seal about a surgical object and to establish a sealing relation with access port 200. Furthermore, such material enables seal anchor 100 to accommodate off-axis motion of the surgical object extending therethrough.

Seal anchor 100 contemplates introduction of various types of instrumentation adapted for insertion through a trocar and/or cannula assembly while maintaining a substantially fluid-tight interface about the instrument to help preserve the atmospheric integrity of a surgical procedure from gas and/or fluid leakage. Examples of instrumentation include, but are not limited to, clip appliers, graspers, dissectors, retractors, staplers, laser probes, photographic devices, endoscopes and laparoscopes, tubes, and the like. Such instruments will collectively be referred to as "instruments" or "instrumentation."

Seal anchor 100 includes proximal and distal end portions 102, 104 and an intermediate portion 106 extending between proximal and distal end portions 102, 104. Seal anchor 100 defines at least one lumen or channel 108 that extends longitudinally between proximal and distal end portions 102, 104. Proximal and distal end portions 102, 104 define substantially planar surfaces. However, proximal and distal end portions 102, 104 may define surfaces that are substantially arcuate to assist in the insertion of seal anchor 100 within tissue. The radial dimension of intermediate portion 106 is appreciably less than those of respective proximal and distal end portions 102, 104. Under such configuration, seal anchor 100 defines an hourglass shape or profile to assist in anchoring seal anchor 100 within tissue when seal anchor 100 is used as a stand-alone device.

Seal anchor 100 is adapted to transition from an expanded condition to a deformed condition to facilitate insertion and securement of the surgical instruments in tissue. Seal anchor 100 is formed of a biocompatible compressible material that facilitates the resilient, reciprocal transitioning of seal anchor 100 between the expanded and deformed conditions thereof. Seal anchor 100 is biased to the initial condition, and thus in the absence of any force applied to seal anchor 100, seal anchor 100 is in the expanded condition.

Figure 10:
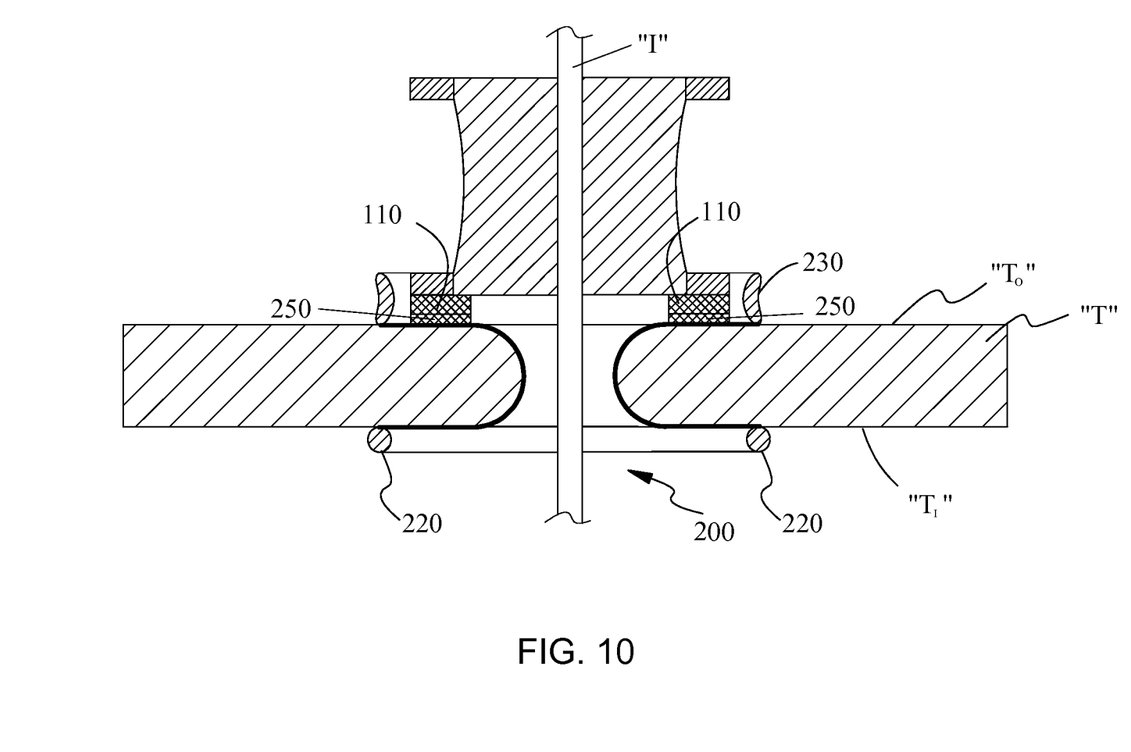
FIG. 10 is a longitudinal cross-sectional view of the surgical access assembly of FIG. 1 secured in a sealing relation to tissue.

Lumen 108 is configured to removably receive a surgical object "I" (FIG. 10). Prior to the insertion of surgical object "I," lumen 108 is in a first state in which lumen 108 defines a first or initial dimension that substantially prevents escape of insufflation gas through lumen 108 in the absence of surgical object "I." Upon insertion of surgical object "I" through lumen 108, lumen 108 transitions to a second state in which lumen 108 defines a second, larger dimension that substantially approximates the diameter of surgical object "I" such that a substantially fluid-tight seal is formed with surgical object "I." In particular, the compressible material comprising seal anchor 100 facilitates the resilient transitioning of lumen 108 between its first closed state and its second state. An example of a seal anchor is disclosed in commonly assigned U.S. patent application Ser. No. 12/939,204, filed on Nov. 4, 2010, the entire contents of which are fully incorporated herein by reference.

Figure 2:
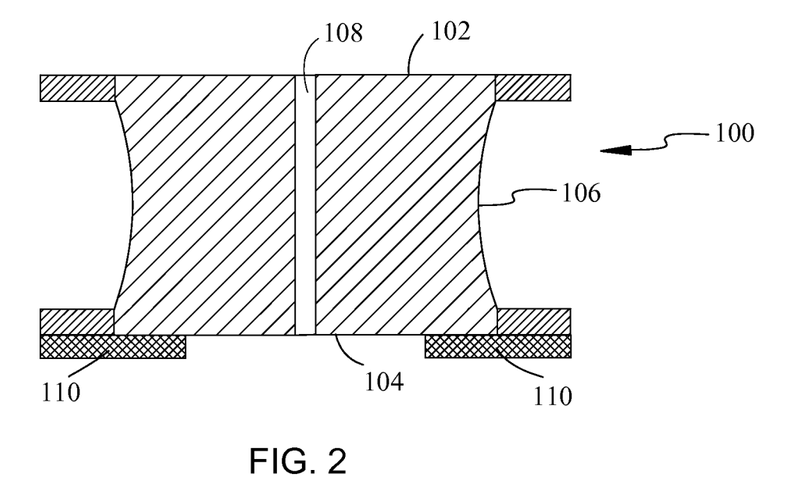
FIG. 2 is a longitudinal cross-sectional view of a seal anchor of the surgical access assembly of FIG. 1 taken along section line 2-2 of FIG. 1 illustrating a longitudinally extending lumen of the seal anchor.

With reference now to FIG. 2, seal anchor 100 further includes an attaching member 110 at distal end portion 104 thereof. Attaching member 110 may be an annular member peripherally arranged about lumen 108. Attaching member 110 detachably couples seal anchor 100 to access port 200, as will be discussed in detail hereinbelow (FIG. 10). Attaching members 110 may include, for example, a refastenable tape or a hook and loop fastener commercially available under the trade name Velcro™. Alternatively, attaching member 110 may include a double-sided adhesive tape to detachably attach seal anchor 100 to access port 200.

Figure 3:
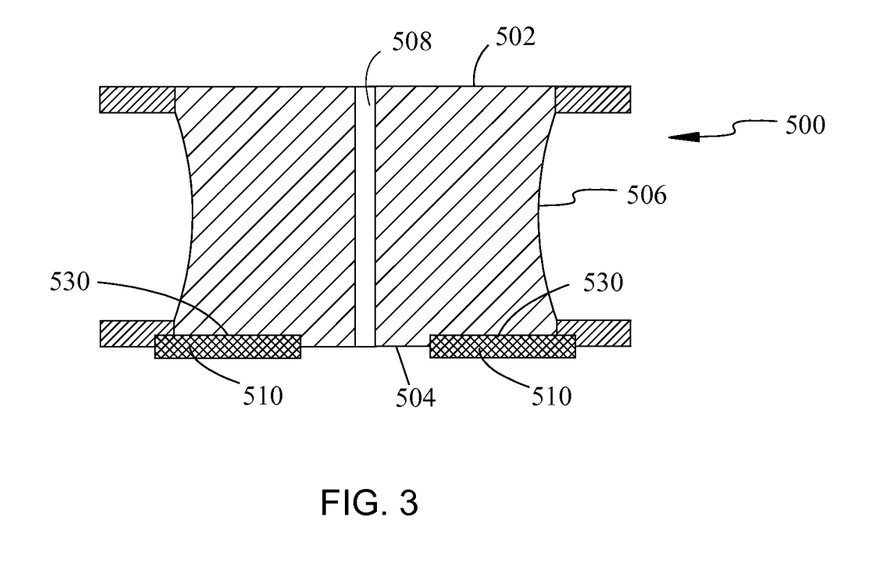
FIG. 3 is a longitudinal cross-sectional view of a seal anchor in accordance with an embodiment of the present disclosure.

With reference to FIG. 3, a seal anchor 500 in accordance with an embodiment of the present disclosure is illustrated. In the interest of brevity, the present embodiment will focus on the differences between seal anchor 500 and the previously described seal anchor 100. Attaching member 510 detachably couples seal anchor 500 to access port 200. Seal anchor 500 includes proximal and distal end portions 502, 504 and an intermediate portion extending between proximal and distal end portions 502, 504. Proximal and distal end portions 502, 504 define substantially planar surfaces. Intermediate portion 506 defines a lumen 508 extending therethrough.

In contrast to seal anchor 100, distal end portion 504 of seal anchor 500 defines a peripherally arranged circumferential groove 530. Attaching member 510 has an annular configuration dimensioned to be disposed in circumferential groove 530. A depth of groove 530 corresponds to a thickness of the material chosen for attaching member 510. In this manner, the effect of the thickness of attaching member 510 on the sealing relation between distal end portion 504 of seal anchor 500 and access port 200 is minimized.

Furthermore, attaching member 510 disposed in groove 530 may be, for example, substantially flush with distal end portion 504 of seal anchor 500. The compressive nature of seal anchor 500 enables the user to press attaching member 510 that is substantially flush with distal end portion 504 of seal anchor 500 against attaching member 250 of access port 200 to enable substantially fluid-tight seal with access port 200.

Attaching member 510 may include, for example, a refastenable tape or a hook and loop fastener commercially available under the trade name Velcro™. Alternatively, attaching member 510 may include a double-sided adhesive tape to detachably attach seal anchor 500 to access port 200.

Figure 4:
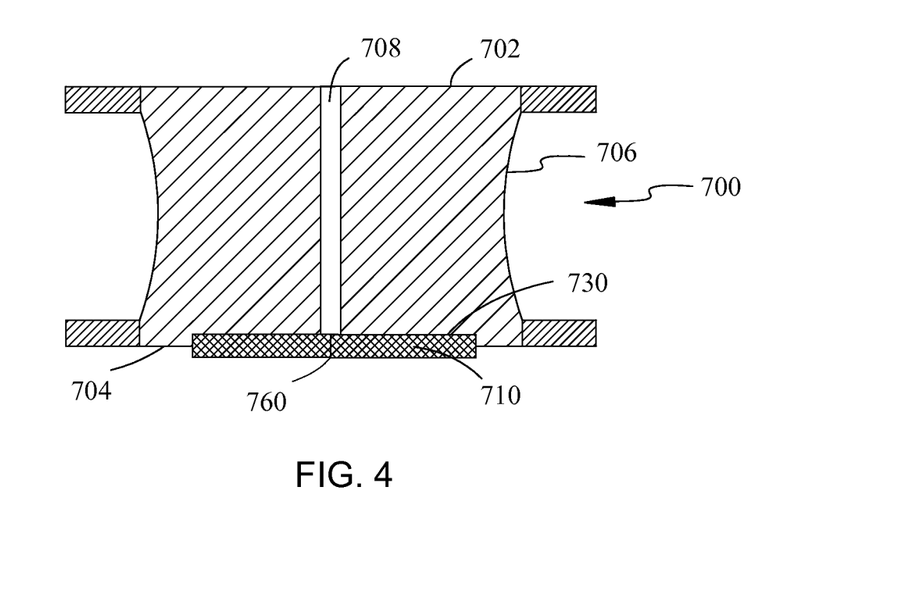
FIG. 4 is a longitudinal cross-sectional view of a seal anchor in accordance with an embodiment of the present disclosure.

With reference now to FIG. 4, a seal anchor 700 in accordance with an embodiment of the present disclosure is illustrated. Attaching member 710 detachably couples seal anchor 700 to access port 200. In contrast to seal anchors 100, 500 discussed hereinabove, seal anchor 700 defines a circular groove 730 at a distal end portion 704 of seal anchor 700. In particular, circular groove 730 extends radially outward from the center of distal end portion 704. Circular attaching member 710 is dimensioned to be disposed in circular groove 730. In addition, attaching member 710 may further define a slit 760 in alignment with lumen 708, to enable passage of surgical instruments "I" therethrough. Under such configuration, seal anchor 700 may provide a greater contact surface with attaching member 250.

Attaching member 710 may include, for example, a refastenable tape or a hook and loop fastener commercially available under the trade name Velcro™. Alternatively, attaching member 710 may include a double-sided adhesive tape to detachably attach seal anchor 700 to access port 200.

Figure 5:
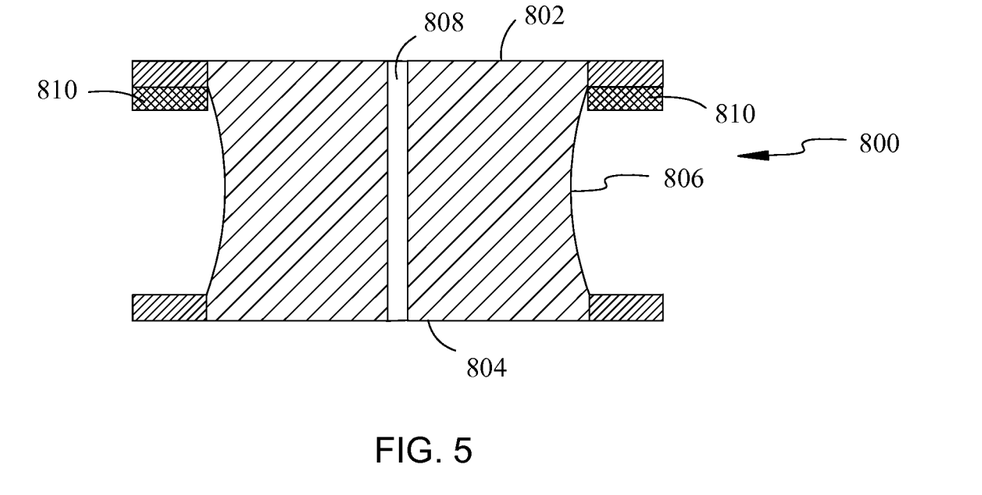
FIG. 5 is a longitudinal cross-sectional view of a seal anchor in accordance with an embodiment of the present disclosure.

With reference now to FIG. 5, a seal anchor 800 in accordance with an embodiment of the present disclosure is illustrated. In contrast to the previously described seal anchors 100, 500, 700, seal anchor 800 includes attaching member 810 disposed adjacent proximal end portion 802. Under such configuration, attaching member 810 enables seal anchor 800 to be detachably attached to access port 200 in a sealing relation, while at least partially inserted through the opening in tissue "T." In this manner, a lower profile of surgical access assembly may be effected. For example, when seal anchor 800 is at least partially inserted through the opening in tissue "T," proximal end portion 802 may be flush with proximal ring 230 of access port 200.

Figure 6:
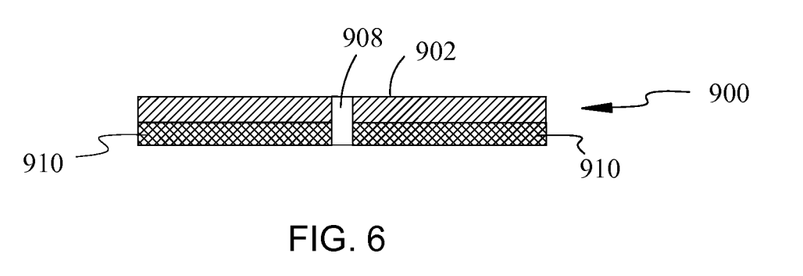
FIG. 6 is a longitudinal cross-sectional view of a seal anchor in accordance with an embodiment of the present disclosure.

It is further contemplated that, a further reduction in profile of surgical access assembly may be effected through a use of, for example, a seal anchor 900, as shown in FIG. 6. Seal anchor 900 includes a proximal end portion 902 and an attaching member 910 in a superposed relation therewith. Proximal end portion 902 and attaching member 910 define a lumen 908 dimensioned for passage of surgical instruments "I" therethrough. In contrast to the previously discussed seal anchors 100, 500, 700, 800, seal anchor 900 does not have intermediate portion 106, 506, 706, 806 which gives seal anchors 100, 500, 700, 800 the hourglass shape or profile. Under such configuration, seal anchor 900 may be disposed entirely within proximal ring 230.

Figure 1A:
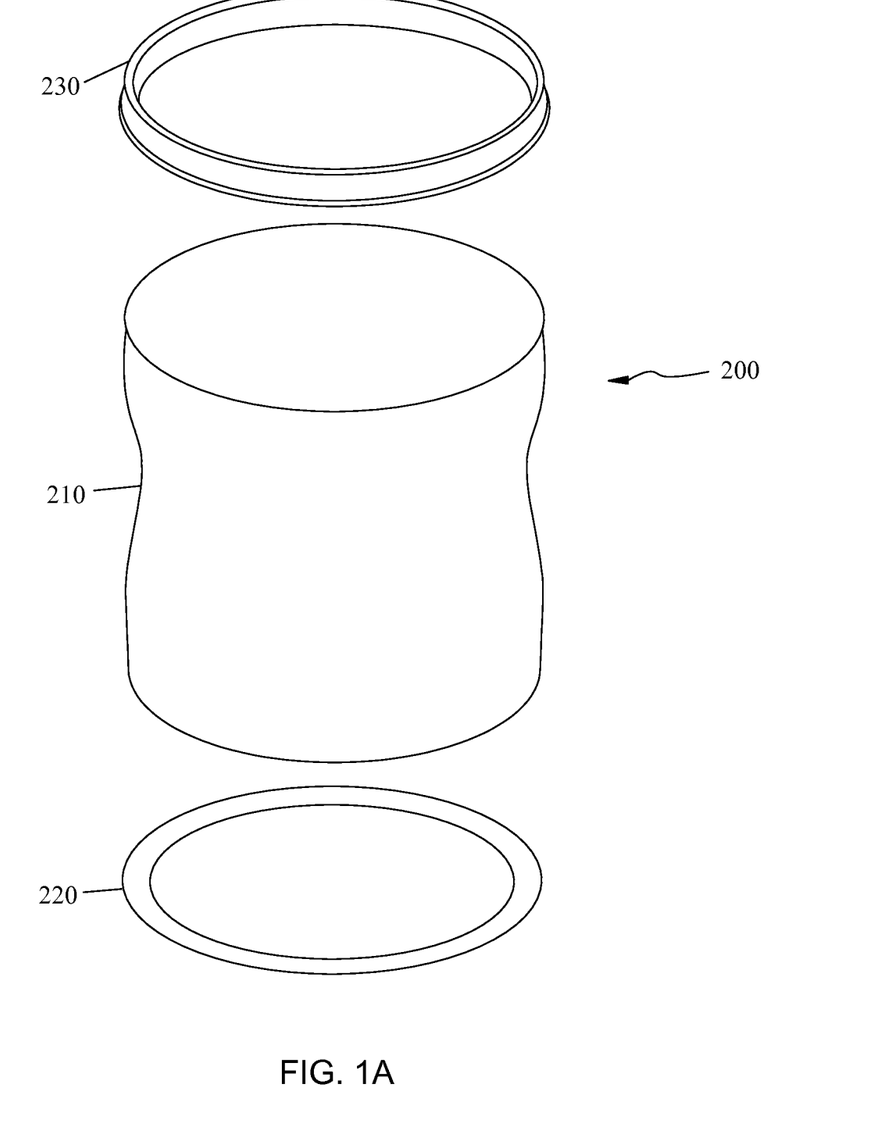
FIG. 1A is an exploded perspective view of an access port of the surgical access assembly of FIG. 1.

With reference back to FIGS. 1 and 1A, access port 200 includes a distal ring 220, a proximal ring 230 and a flexible sleeve 210 having a length extending between distal and proximal rings 220, 230. Distal and proximal rings 220, 230 are formed of relatively flexible materials to facilitate compression and expansion of distal and proximal rings 220, 230. For example, distal and proximal rings 220, 230 may be made from an elastomer such as polyurethane, polyethylene, silicone, and the like. The resilient nature of distal and proximal rings 220, 230 allows distal and proximal rings 220, 230 to return to their normal, substantially annular configuration. Furthermore, distal and proximal rings 220, 230 are adapted to engage the walls of tissue defining the body cavity to further facilitate securement of access port 200 within the body tissue. For example, distal ring 220 engages the internal peritoneal wall $T_I$, and proximal ring 230 engages the outer epidermal tissue $T_O$ (FIG. 9).

Figure 7:
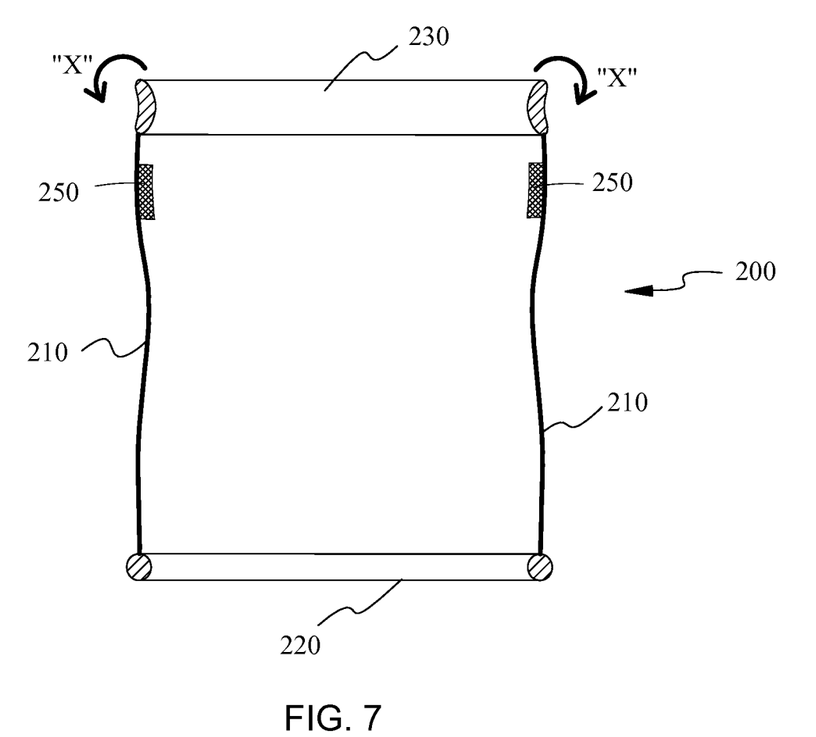
FIG. 7 is a longitudinal cross-sectional view of the access port of the surgical access assembly of FIG. 1.
Figure 8:
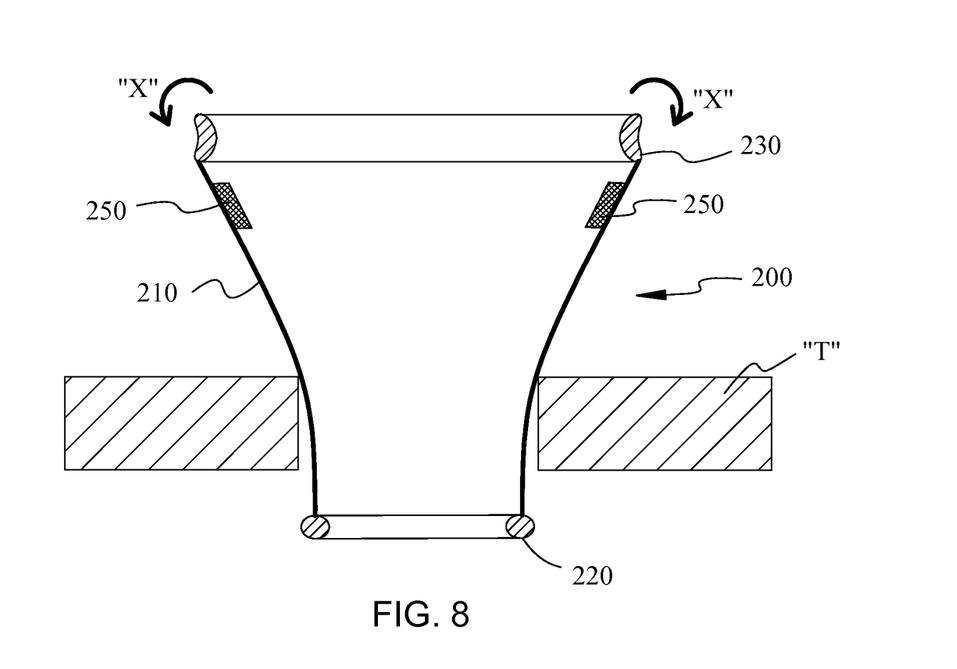
FIGS. 8 and 9 are longitudinal cross-sectional views of the access port of FIG. 7 illustrating insertion of the access port in tissue.
Figure 9:
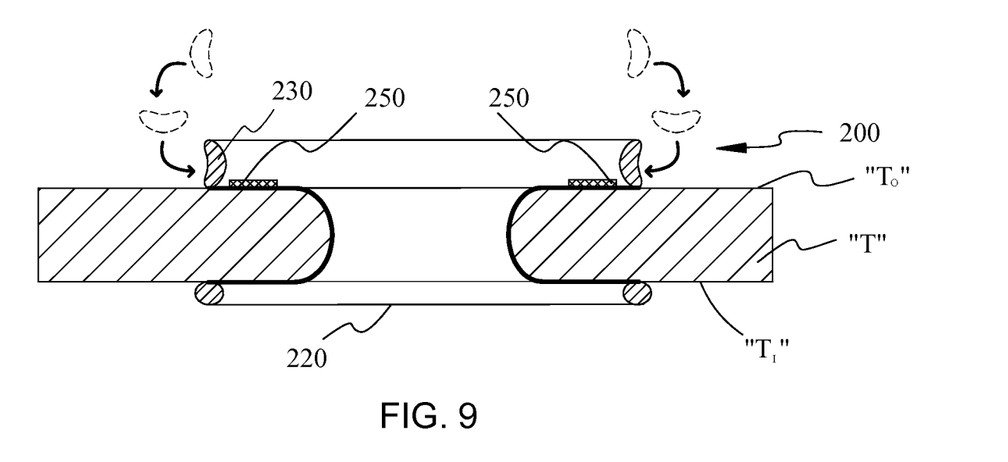

With reference now to FIG. 7-9, sleeve 210 has elastomeric properties to facilitate securement of access port 200 with the opening. Proximal ring 230 is rollable to gather flexible sleeve 210 around proximal ring 230. For example, proximal ring 230 is rollable in the outward direction (as shown by arrow "X") to shorten sleeve 210 and in the inward direction to lengthen the sleeve 210, or vice versa. Sleeve 210 may be shortened such that proximal ring 220 engages the outer epidermal tissue $T_O$ adjacent the opening in tissue "T" and distal ring 230 positioned in the body cavity engages internal peritoneal wall $T_I$ (FIG. 9). In this manner, access port 200 is securely fixed to the tissue.

With continued reference to FIG. 7-9, proximal ring 230 has a kidney-shaped cross-sectional profile. Kidney-shaped cross-section facilitates rolling of sleeve 210 about proximal ring 230 and inhibits unrolling of sleeve 210 over proximal ring 230 by providing a flattened edge disposed on the outer epidermal tissue $T_O$. Distal ring 220, on the other hand, may be an O-ring having a circular cross-section. However, other cross-sectional profiles are also contemplated for proximal and distal rings 230, 220. It is also envisioned that the O-ring may be an inflatable balloon.

With particular reference to FIG. 9, distal and proximal rings 220, 230 can vary in size. The dimensions of distal and proximal rings 220, 230 may be selectively chosen to be greater than that of the opening (FIG. 9). In this manner, distal and proximal rings 220, 230 may have sufficient footing to maintain elastic sleeve 210 that has been stretched and retained at a distance greater than the natural distance.

By having diameters of distal and proximal rings 220, 230 larger than that of the opening, access port 200 is adapted to dilate the opening to provide a desired diameter and provides positive securement of access port 200 in the opening. More retraction is possible through shortening of sleeve 210 by rolling proximal ring 230 outward, while less retraction is possible by rolling proximal ring 230 inward.

With reference back to FIG. 7, access port 200 further includes an attaching member 250 corresponding to attaching member 110 of seal anchor 100. For example, attaching members 110, 250 may each include a refastenable tape or a hook and loop fastener commercially available under the trade name Velcro™. Alternatively, at least one of attaching members 110, 250 may include a double-sided adhesive tape to detachably attach seal anchor 100 to access port 200. Attaching member 250 is circumferentially disposed on an inner surface of sleeve 210. In particular, attaching member 250 is disposed adjacent proximal ring 230. Under such configuration, when sleeve 210 is rolled about proximal ring 230 to place proximal ring 230 in contact with the outer epidermal tissue $T_O$ or to retract the wound, attaching member 250 is at least partially disposed on the outer epidermal tissue $T_O$ (FIG. 9). At this time, attaching member 110 of seal anchor 100 is aligned with and disposed on attaching member 250 of access port 200. Attaching members 110, 250 enable seal anchor 100 to be detachably attached to access port 200 in a sealing relation. While seal anchor 100 has been used in describing the sealing relation between seal anchor 100 and access port 200, seal anchors 500, 700, 800, 900 may be used with access port 200.

In use, the peritoneal cavity (not shown) is insufflated with a suitable biocompatible gas such as, e.g., $CO_2$ gas, such that the cavity wall is raised and lifted away from the internal organs and tissue housed therein, thereby providing greater access thereto. The insufflation may be performed with an insufflation needle or similar device, as is conventional in the art. Either prior or subsequent to insufflation, an opening is made in tissue "T," the dimensions of which may be varied dependent upon the nature of the procedure.

Prior to the insertion of access port 200 within tissue, access port 200 is in its expanded condition in which the dimensions thereof inhibit the insertion of access port 200 into tissue tract. To facilitate insertion, the user transitions distal ring 220 into the compressed condition by, e.g., squeezing distal ring 220, as shown in FIG. 8. Subsequent to its insertion, distal ring 220 is disposed beneath tissue "T." At this time, proximal ring 230 may be rolled in the direction of arrow "X," as shown in FIG. 8, such that distal ring 220 engages internal peritoneal wall $T_I$ and proximal ring 230 engages the outer epidermal tissue $T_O$ to secure access port 200 within the opening in tissue "T," as shown in FIG. 9. Depending on the nature of the procedure being performed, the opening in the wound may be retracted by rolling sleeve 210 about proximal ring 230. At this time, attaching member 250 is at least partially disposed on the outer epidermal tissue $T_O$.

Then, seal anchor 100 is at least partially placed within proximal ring 230 of access port 200. In particular, attaching member 110 of seal anchor 100 is directly aligned with and disposed on attaching member 250, whereby seal anchor 100 is detachably secured to access port 200 while providing a sealing relation therebetween. Prior to the insertion of surgical object, lumen 108 defines a first or initial dimension that substantially prevents escape of insufflation gas through lumen 108 in the absence of surgical object "I." Upon insertion of surgical object "I" through lumen 108, lumen 108 transitions to a second state in which lumen 108 defines a second, larger dimension that substantially approximates the diameter of surgical object "I" such that a substantially fluid-tight seal is formed with surgical object "I."

Thereafter, one or more surgical objects may be inserted through lumen 108 of seal anchor 100, as shown in FIG. 10. With surgical instruments "I" inserted through lumen 108 and into the body cavity of the patient, the user may swivel or rotate surgical instrument "I" to a desired orientation with respect to tissue "T." During the surgical procedure, surgical instrument "I" and seal anchor 100 may be removed from access port 200, to enable passage of the surgeon's hand through the wound to access the body cavity of the patient. Upon completing the surgical procedure, the user may remove the surgical access assembly 10 from the opening of the patient.

Figure 11:
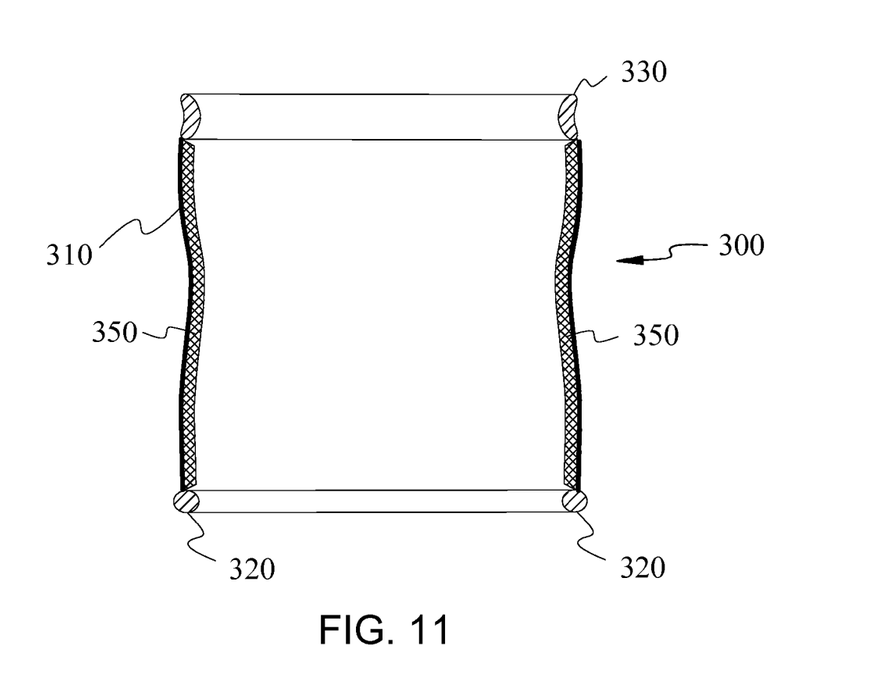
FIGS. 11-13 are longitudinal cross-sectional views of an access port in accordance with another embodiment of the present disclosure.
Figure 12:
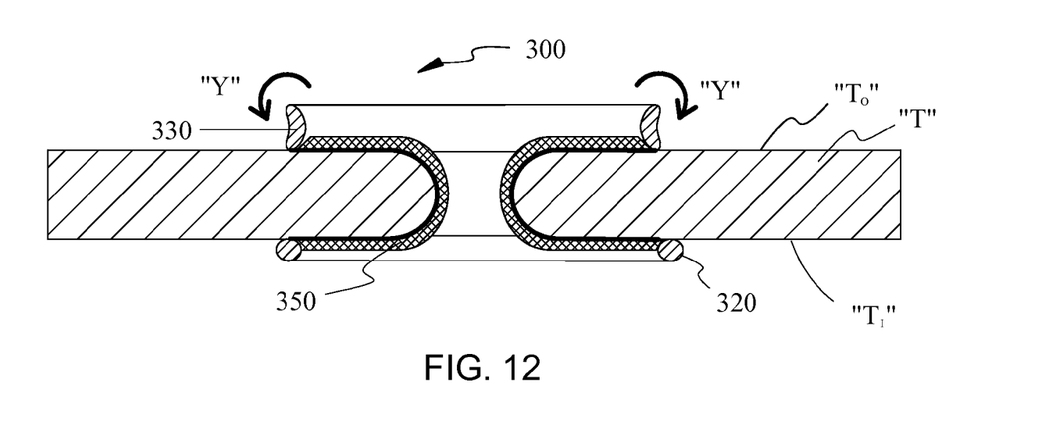
Figure 13:
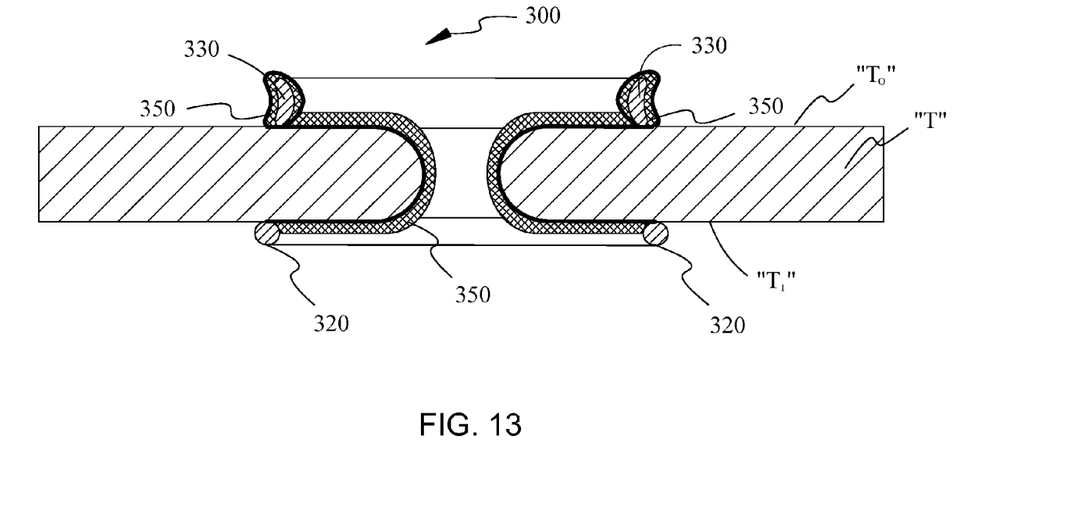

With reference now to FIGS. 11-13, an access port 300 in accordance with an embodiment of the present disclosure is illustrated. In the interest of brevity, the present embodiment will focus on the differences between access port 300 and the previously described access port 200. Access port 300 includes a distal ring 320, proximal ring 330, and a flexible sleeve 310 having a length extending between distal and proximal rings 320, 330. Distal and proximal rings 320, 330 are formed of relatively flexible materials to facilitate compression and expansion of distal and proximal rings 320, 330. Access port 300 further includes an attaching member 350 corresponding to attaching member 110 of seal anchor 100. Attaching member 350 may be a refastenable tape or a hook and loop fastener commercially available under the trade name Velcro™. Alternatively, attaching members 110, 350 may include a double-sided adhesive tape to detachably attach seal anchor 100 to access port 300.

In particular, attaching member 350 is disposed on an inner wall of sleeve 310, and extends substantially the entire length of sleeve 310. In this manner, regardless of the amount of retraction desired (by rolling sleeve 310 about proximal ring 330), at least a portion of attaching member 350 is disposed on the outer epidermal tissue $T_O$ to enable securement of seal anchor 100 thereon (FIGS. 12 and 13), while providing a sealing relation therebetween. However, it is contemplated that the length of attaching member 350 may be tailored to meet the particular need of a surgical procedure being performed. The operation and use of access port 300 is substantially similar to access port 200. Thus, the operation and use of access port will not be discussed herein in the interest of brevity.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A surgical access assembly comprising:
   an access port including first and second rings and a sleeve extending between the first and second rings, the sleeve including an inner surface having an attaching member, the sleeve selectively rollable to adjust a position of the attaching member on the sleeve; and
   a seal anchor adapted to be at least partially disposed in the access port, the seal anchor defining a lumen extending therethrough, the seal anchor including a base portion configured to detachably engage the attaching member of the access port, the seal anchor transitionable between an expanded condition and a deformed condition, wherein the base portion of the seal anchor includes a second attaching member adapted to be detachably attached to the attaching member of the access port, the second attaching member of the seal anchor disposed distal of the lumen of the seal anchor and in registration with the lumen of the seal anchor.

2. The surgical access assembly according to claim 1, wherein the second attaching member of the seal anchor is a refastenable tape.

3. The surgical access assembly according to claim 1, wherein the second attaching member of the seal anchor is a hook and loop fastener.

4. The surgical access assembly according to claim 1, wherein the base portion of the seal anchor defines a groove configured to receive the second attaching member of the seal anchor therein.

5. The surgical access assembly according to claim 1, wherein the lumen of the seal anchor is dimensioned to receive surgical instruments therethrough.

6. The surgical access assembly according to claim 1, wherein the second attaching member of the seal anchor defines a slit in alignment with the lumen.

7. The surgical access assembly according to claim 1, wherein the attaching member of the access port is a refastenable tape.

8. The surgical access assembly according to claim 1, wherein the attaching member of the access port is a hook and loop fastener.

9. The surgical access assembly according to claim 1, wherein the attaching member of the access port is an adhesive tape.

10. The surgical access assembly according to claim 1, wherein the attaching member of the access port is an annular ring disposed on the inner surface of the sleeve.

11. The surgical access assembly according to claim 1, wherein the first ring of the access port has a kidney shaped cross-sectional profile.

12. The surgical access assembly according to claim 11, wherein the second ring of the access port is an O-ring.

13. The surgical access assembly according to claim 12, wherein the second ring is an inflatable balloon.

14. The surgical access assembly according to claim 1, wherein the first and second rings are elastic.

15. The surgical access assembly according to claim 1, wherein the attaching member of the access port extends along a length of the sleeve of the access port.

16. The surgical access assembly according to claim 1, wherein the sleeve is made of an elastic material.

17. The surgical access assembly according to claim 1, wherein the seal anchor is made of a compressible material.

18. The surgical access assembly according to claim 1, wherein the second ring is an O-ring.

* * * * *